(12) United States Patent
Linder

(10) Patent No.: US 7,687,032 B2
(45) Date of Patent: Mar. 30, 2010

(54) FILTER ASSEMBLY FOR MOLECULAR TESTING

(75) Inventor: James Linder, Acton, MA (US)

(73) Assignee: Cytyc Corporation, Marlborough, MA (US)

( * ) Notice: Subject to any disclaimer, the term of this patent is extended or adjusted under 35 U.S.C. 154(b) by 1364 days.

(21) Appl. No.: 11/123,832

(22) Filed: May 5, 2005

(65) Prior Publication Data

US 2005/0247646 A1 Nov. 10, 2005

Related U.S. Application Data

(60) Provisional application No. 60/569,386, filed on May 6, 2004.

(51) Int. Cl.
*B01L 3/02* (2006.01)
(52) U.S. Cl. .................................................. 422/100
(58) Field of Classification Search ............... 422/101, 422/100
See application file for complete search history.

(56) References Cited

U.S. PATENT DOCUMENTS

| | | | |
|---|---|---|---|
| 5,143,627 A | 9/1992 | Lapidus et al. | |
| 5,240,606 A | 8/1993 | Lapidus et al. | |
| 5,269,918 A | 12/1993 | Lapidus et al. | |
| 5,282,978 A | 2/1994 | Polk, Jr. et al. | |
| 5,364,597 A | 11/1994 | Polk, Jr. et al. | |
| 5,772,818 A | 6/1998 | Polk, Jr. et al. | |
| 5,833,927 A | 11/1998 | Raybuck et al. | |
| 5,942,700 A | 8/1999 | Radcliffe et al. | |
| 6,318,190 B1 | 11/2001 | Radcliffe et al. | |
| 6,572,824 B1 | 6/2003 | Ostgaard et al. | |
| 2002/0040610 A1 | 4/2002 | Radcliffe et al. | |
| 2003/0207456 A1 | 11/2003 | Ostegaard et al. | |

FOREIGN PATENT DOCUMENTS

EP 0589293 3/1994

OTHER PUBLICATIONS

PCT International Search Report for PCT/US2005/015603, Applicant: Cytyc Corporation, Forms PCT/ISA/210 and 220, dated Aug. 30, 2005 (7 pages).
PCT Written Opinion of the International Search Authority for PCT/US2005/015603, Applicant: Cytyc Corporation, Forms PCT/ISA/237, dated Aug. 30, 2005 (7 pages).

*Primary Examiner*—Walter D Griffin
*Assistant Examiner*—Bobby Ramdhanie
(74) *Attorney, Agent, or Firm*—Vista IP Law Group LLP

(57) ABSTRACT

A cytological material sample collection device comprises a cylinder having a longitudinal bore extending there through. The sample collection device further comprises a filter membrane configured for collecting a layer of cytological material when the bore is subjected to negative pressure. The sample collection device further comprises a drip guard disposed on the cylinder proximal to the membrane. The drip guard may include at least one access port in fluid communication with the bore. The sample collection device may further comprise a chuck that selectively mates with the cylinder, so that, after usage of the sample collection device, the cylinder can be discarded, while the chuck can be reused with subsequent cylinders.

5 Claims, 3 Drawing Sheets

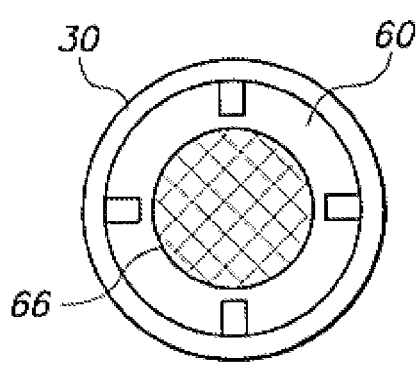
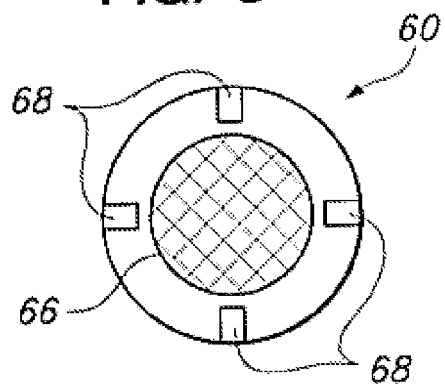
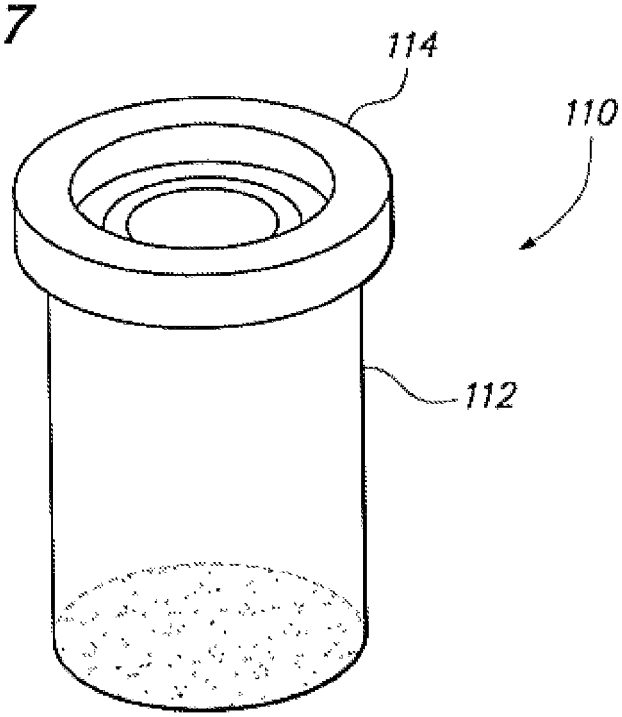

FILTER ASSEMBLY FOR MOLECULAR TESTING

RELATED APPLICATION

This application claims priority from provisional U.S. patent application Ser. No. 60/569,386, filed May 6, 2004.

FIELD OF THE INVENTION

The invention pertains to the preparation of cytological specimens, and more specifically, to a filter assembly used for collecting and applying a cytological specimen on a biological slide.

BACKGROUND

Cytology is a branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "pap smear" test, in which cells are scraped from a woman's cervix and analyzed in order to detect the presence of abnormal cells—a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions may be applied to the cells on the glass slide for preserving the specimen for archival purposes and for facilitating examination.

It is generally desirable that the cells on the slide have a proper spatial distribution, so that individual cells can be examined. A monolayer of cells is typically preferred. Accordingly, preparing a specimen from a fluid sample containing many cells typically requires that the cells first be separated from each other by mechanical dispersion, fluidic shear, or other techniques so that a thin, monolayer of cells can be collected and deposited on the slide. In this manner, the cytotechnologist can more readily discern abnormal cells. The cells are also able to be counted to ensure that an adequate number of cells have been evaluated.

Certain methods and apparatus for generating a thin monolayer of cells on a biological slide advantageous for visual examination are disclosed in U.S. Pat. Nos. 5,143,627, 5,240,606, 5,269,918, and 5,282,978, the disclosures of which are expressly incorporated herein by reference.

Two commercially successful apparatus manufacturing in accordance with the teachings of one or more of these patents has been marketed as the ThinPrep™2000 and ThinPrep™ 3000 Processors (the "ThinPrep™ Processor") by Cytyc Corporation, located in Boxborough, Mass. During this commercial process, a gynecologic sample is collected using a broom-type or cytobrush/spatula cervical sampling device. Then, the sampling device is rinsed into a vial containing PreservCyt® transport medium. The sample vial is then capped, labeled, and sent to a laboratory for slide preparation. At the laboratory, the vial is placed into the ThinPrep™ Processor, which under control of the instrument's microprocessor, performs the following procedures.

First, the ThinPrep™ Processor uses a portable sample collection device to disperse and collect cells from the liquid sample contained within the sample vial. The sample collection device comprises a disposable plaster filter cylinder, which is introduced by the ThinPrep™ Processor into the liquid sample, and a non-disposable plastic filter cap, which the ThinPrep™ Processor uses to interface with the filter cylinder. The ThinPrep™ Processor generates a negative pressure pulse that draws fluid through the sample collection device, and collects a thin, even layer of diagnostic cellular material on the filter cylinder. The ThinPrep™ Processor constantly monitors the rate of flow through the sample collection device during the collection process to prevent the cellular presentation from being too scant or too dense. The ThinPrep™ Processor then generates a positive pressure pulse that deposits the cellular material on a glass slide. The slide is then analyzed to determine whether the sample is positive or negative for a specified disease.

During the sample collection process, a portion of the liquid sample often comes in contact with the filter cap. Because the filter cap is designed to be non-disposable, and thus reused, it must be thoroughly washed to remove all of the liquid sample that adheres to the filter cap. If the filter cap is not properly washed, cells, microorganisms, proteins and other substances can be transferred from one sample to a subsequent sample, thereby cross-contaminating the samples. As a result, the diagnostic results of each specimen may be compromised. To prevent such contamination, a thorough sterilization protocol is currently followed by technicians who operate the ThinPrep™ Processors.

SUMMARY OF THE INVENTION

In accordance with a one aspect of the invention, a cytological sample collection device is provided. The sample collection device comprises a cylinder having a longitudinal bore extending therethrough. The sample collection device further comprises a filter membrane mounted to the distal end of the cylinder. The membrane has pores that are in fluid communication with the bore. In one embodiment, the membrane is configured for collecting a layer of cytological material when the bore is subjected to negative pressure. The sample collection device further comprises a drip guard disposed on the cylinder proximal to the membrane. The drip guard and cylinder can be integrated as a unibody structure, or may be discrete elements that are suitably mounted to each other. Preferably, the drip guard is disposed within the bore of the cylinder. The drip guard includes at least one access port in fluid communication with the bore. In this manner, pressure within the entire longitudinal bore will be equalized in order to communicate pressure changes applied to the proximal end of the cylinder to effect the desired result at the distal end of the cylinder, e.g., collecting the cytological material from a specimen or depositing the cytological material on a biological slide.

In one embodiment, the sample collection device comprises a chuck disposed on the proximal end of the cylinder. In this case, the chuck has a bore in fluid communication with the bore of the cylinder, and an enlarged boss having a recessed cylindrical cavity in fluid communication with the bore of the cap. The recessed cavity is configured for receiving an external coupling member from, e.g., a sample processor. In this manner, the sample processor can move the sample collection device, as well as actuate the sample collection device to collect and/or deposit the sample. The chuck can be selectively mateable with the cylinder, so that, after usage of the sample collection device, the cylinder can be discarded, while the chuck can be reused with subsequent cylinders. Because the drip guard will prevent any contaminated liquid on the chuck from contacting the filter membrane, any concern regarding the usage of the chuck with multiple cylinders is minimized.

In accordance with a second aspect of the invention, another cytological sample collection device is provided. The sample collection device comprises a body having a cylinder, an enlarged boss formed on the cylinder, and a longitudinal bore extending through the cylinder and boss. The boss has a recessed cavity in fluid communication with the bore. The recessed cavity is configured for receiving an external coupling member from, e.g., a sample processor. The sample collection device further comprises a filter membrane disposed on the cylinder. The membrane has pores in fluid communication with the bore. Because the boss and cylinder are integrated as a unibody structure-preferably composed of a relatively inexpensive material, the entire sample collection device can be discarded. In this regard, no drip guard is needed, since no portion of the sample collection device will be reused.

In accordance with a third aspect of the invention, a method of collecting cytological material is provided. The method comprises introducing a filter cylinder within a specimen that contains a liquid and cytological material. The method further comprises mating a chuck with the filter cylinder, and applying negative pressure within the filter cylinder via the chuck. As a result, a layer of the cytological material, and preferably a monolayer of cells, is collected on the exterior of the filter cylinder. The method further comprises preventing any liquid that drips from the inner surface of the chuck to contact the exterior of the filter cylinder, e.g., by moving through a filter membrane. By way of non-limiting example, the previously described drip guard can be used. In this manner, cross-contamination of samples is avoided when reusing the chuck on subsequent filter cylinders. The method may optionally comprise applying positive pressure within the filter cylinder via the chuck in order to deposit the layer of cytological material on a biological slide.

BRIEF DESCRIPTION OF THE DRAWINGS

The drawings illustrate the design and utility of embodiments of the invention, in which similar elements are referred to by common reference numerals, and in which:

FIG. 5 is a top view of the filter cylinder of FIG. 4;

FIG. 6 is a top view of a drip guard used in the filter cylinder of FIG. 4; and

FIG. 7 is a perspective view of an alternative sample collection device that can be used in the sample collection system of FIG. 1.

DESCRIPTION OF THE ILLUSTRATED EMBODIMENTS

Figure 1:
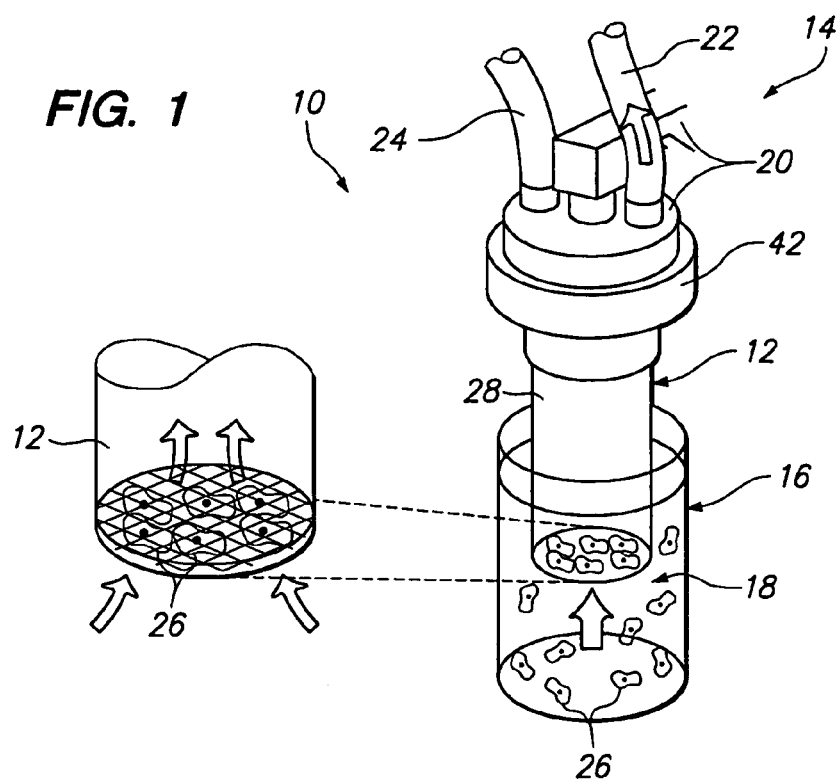
FIG. 1 is a perspective view of a cytological sample collection system constructed in accordance with one embodiment of the invention.

Referring to FIG. 1, a sample collection system 10 constructed in accordance with one embodiment of the invention will now be described in detail. The sample collection system 10 generally comprises a sample collection device 12, a sample processor 14, and a container 16 for holding a liquid sample 18 and making it available to the sample collection device 12.

The container 16 can be any structure suitable for holding a liquid material and for providing access to the liquid material by the sample collection device 12. The container 16 is commonly a sterilized plastic container suited for holding a biological sample and for disposal after the liquid sample is processed by the sample processor 14. The liquid sample can comprise aqueous preservation solution that contains tissue cells. Alternatively, the liquid sample may contain other biological materials, such as scrapings or aspirates.

In the illustrated embodiment, the sample processor 14 uses a pneumatic particle collection technique to draw a portion of the liquid sample 18 within sample collection device 12. Particles dispersed within the liquid sample 18, and in particular cells 26, collect onto the exterior of the sample collection device 12, which can subsequently be applied to a biological slide (not shown). The sample processor 14 is also preferably capable of depositing the particles collected on the sample collection device 12 onto the slide. Preferably, the sample processor 14 is an automated processor, such as the ThinPrep™ Processors previously mentioned herein.

In order to mechanically interface with the sample collection device 12, the sample processor 14 comprises a coupling mechanism 20 that mates with the top portion of the sample collection device 12, as will be described in further detail below. The sample processor 14 also comprises two conduits 22 and 24, the distal ends of which extend through coupling mechanism 20 into fluid communication with the interior of the sample collection device 12. The proximal ends of the conduits 22 and 24 are connected to the pneumatic source (not shown) of the sample processor 14. In this manner, the sample processor 14 can apply negative pressure pulses to the interior of the sample collection device 12 via the conduit 22 in order to collect particles from the liquid sample 18, and apply positive pressure pulses to the interior of the sample collection device 12 via the conduit 24 in order to dispense the collected particles onto the slide.

For purposes of brevity in illustration and description, only the coupling mechanism 20 and conduits 22 and 24 of the sample processor 14 are shown. The structure and functionally of such types of sample processors are described in greater detail in U.S. Pat. Nos. 6,318,190 and 6,572,824, which have previously been incorporated herein by reference.

Figure 2:
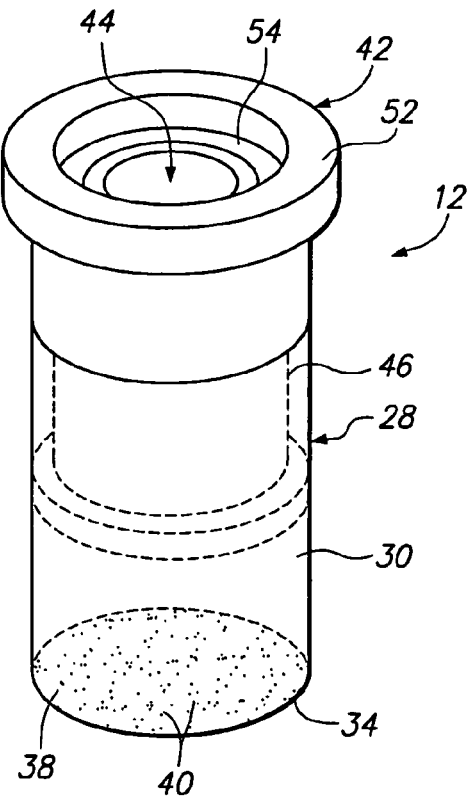
FIG. 2 is a perspective view of a sample collection device used in the sample collection system of FIG. 1.
Figure 4:
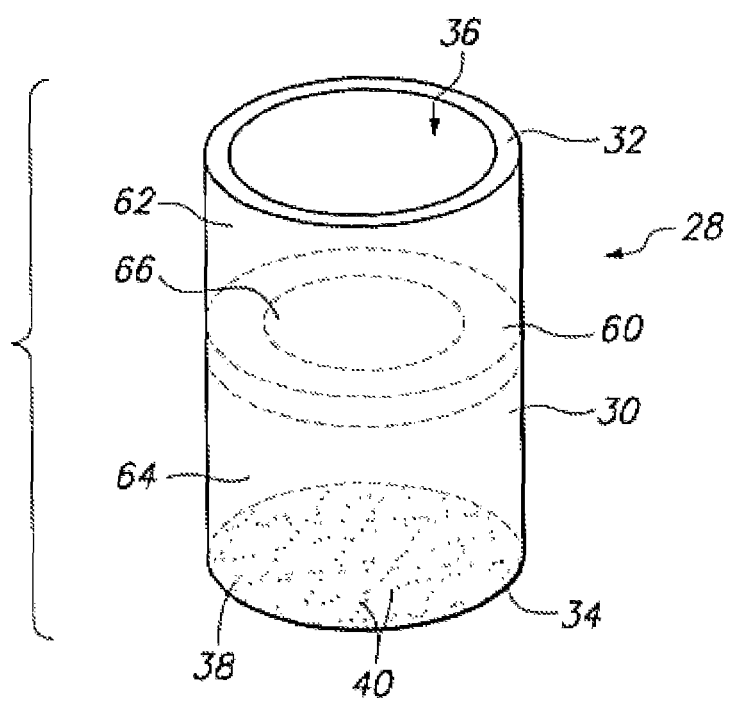
FIG. 4 is a perspective view of a filter cylinder used in the sample collection device of FIG. 2.

Referring to FIGS. 2 and 4, the sample collection device 12 will now be described in greater detail. The sample collection device 12 comprises a filter cylinder 28 having a cylindrical sidewall 30 with a proximal rim 32 and a distal rim 34, and a bore 36 extending longitudinally within the cylindrical sidewall 30 between the rims 32 and 34. The cylindrical sidewall 30 can be composed of any suitable material, but preferably is composed of a relatively inexpensive material, such as polystyrene, so that it can be disposed of after use.

The filter cylinder 28 further comprises a filter membrane 38 mounted to the distal rim 34 of the cylindrical wall 30, such that pores 40 within the membrane 38 are in fluid communication with the bore 36 within the cylindrical wall 30. The filter membrane 38 can be mounted to the distal rim 34 in any suitable manner, including thermal bonding, ultrasonic bonding, or solvent bonding. The filter membrane 38 can be composed of a polycarbonic film having a porosity selected for collecting particles of a particular size from the liquid sample 18 (shown in FIG. 1). For example, the pore size can be approximately 0.2 to 20 microns. One such membrane is a polycarbonate membrane marketed by Nuclepore Corporation in Pleasanton, Calif. Other filter membranes can be formed from materials including cellulose, nylon, polyester, Teflon®, or any other suitable material. The filter membrane 38 is preferably disposed on the distal rim 34 of the cylindrical sidewall 30 in a planar fashion, such that the cytological material that has been collected on the filter membrane 38 can be efficiently transferred to the slide as a monolayer of cells. Further details regarding the construction and use of such filters are disclosed in U.S. Pat. Nos. 5,364,597, 5,772,818, and 5,942,700, the entire disclosures of which are expressly incorporated by reference herein.

Figure 3:
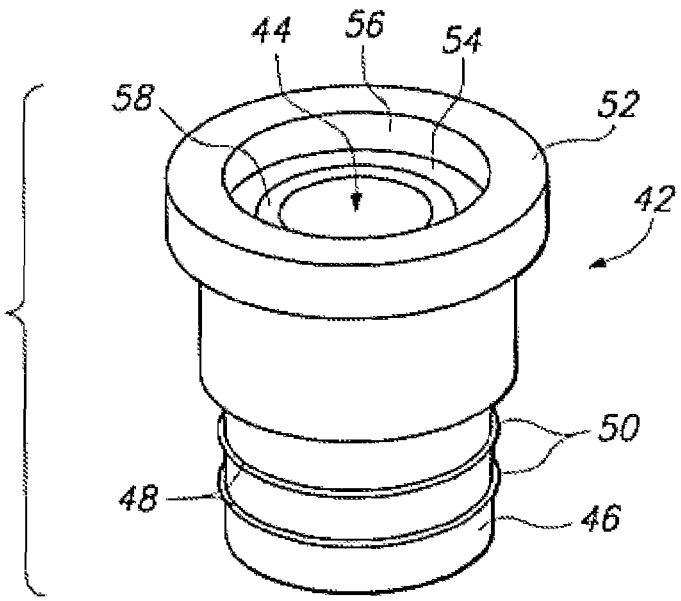
FIG. 3 is a perspective view of a chuck used in the sample collection device of FIG. 2.

Referring further to FIG. 3, the sample collection device 12 further comprises a chuck 42 that selectively mates with the filter cylinder 30. In particular, the chuck 42 has a longitudinal bore 44 is in fluid communication with the bore 36 of the filter cylinder 30 when the chuck 42 is mated with the filter cylinder 30. The chuck 42 further comprises a cylindrical insert 46 (shown in phantom in FIG. 2), which is sized to snugly fit within the proximal end of the filter cylinder 28. The exterior surface of the cylindrical insert 46 comprises a pair of annular recesses 48 in which there is disposed a respective pair of O-ring seals 50. In this manner, the cylindrical insert 46 can sealingly engage the inner surface of the cylindrical sidewall 30 to prevent any pressure leaks in or out of the filter cylinder 30.

The chuck 42 further comprises an enlarged boss 52 formed at the proximal end of the cylindrical insert 46. The boss 52 comprises a recessed cavity 54 that is sized to snugly receive the cylindrical portion of the coupling mechanism 20 of the sample processor 14. The bottom surface of the recessed cavity 54 comprises a recess 56 that is circumferentially disposed around the bore 44. An O-ring seal 58 is disposed within the recess 56, so that the cylindrical portion of the coupling mechanism 20 sealingly mates with the recessed cavity 54, thereby preventing any pressure leaks between the chuck 42 and the coupling mechanism 20.

Thus, it can be appreciated dint the chuck 42 functions to allow the sample processor 14 to mechanically and operationally interface with the filter cylinder 28. Specifically; after the coupling mechanism 20 is mated with the chuck 42 and prior to the littering process, the sample processor 14 may move and introduce the filter cylinder 28 into the container 16 and rapidly rotate the sample collection device 12 to actuate the liquid sample 18 and break-up clumps of particles that may exist within the liquid sample 18.

During the filtering process, the chuck 42 functions as an interface through which the sample processor 14 applies negative and positive pressure pulses to the filter cylinder 28. That is, the pneumatic source of the sample processor 14 may generate negative pressure pulses, which travel through the conduit 22, through the bore 44 of the chuck 42, and into the bore 36 of the filter cylinder 28, thereby creating a negative pressure differential between the bore 36 and the exterior of the filter cylinder 28 that causes a portion of the liquid sample 18 to pass through the filter membrane 38. As a result, a layer of cytological material, and preferably a monolayer of cells, is collected on the distal surface of the filter membrane 38.

After the filtering process, the sample processor 14 can remove the filter cylinder 28 from the container 16, and then place the distal surface of the filter cylinder 28, i.e., the filter membrane 38, in contact with a biological slide. The pneumatic source of the sample processor 14 may then generate a positive pressure pulse, which travels through the conduit 24, through the bore of the chuck 42, and into the bore 36 of the filter cylinder 28, thereby creating a positive pressure differential between the bore 36 and the exterior of the filter cylinder 28 that causes the liquid sample 18 collected on the filter membrane 38 to be deposited on the slide as a single cell layer.

Because there is a danger that any liquid contamination on the chuck 42, which may originate from another filter cylinder with which the chuck 42 has been previously mated, can contaminate the cytological material collected on the filter cylinder 28, the filter cylinder 28 further comprises a circular drip guard 60 mounted within the bore 36 of the filter cylinder 28. In the illustrated embodiment, the drip guard 60 is bonded to the inner surface of the cylindrical sidewall 30 using suitable means, such as thermal, solvent, or ultrasound bonding. Alternatively, the drip guard 60 can be formed with the filter cylinder 28 as a unibody structure. In the illustrated embodiment, the drip guard 60 is mounted distal to the proximal rim 32, thereby providing enough clearance for the cylindrical insert 46 of the chuck 42 to be inserted within the proximal end of the filter cylinder 28.

The drip guard 60 divides the bore 36 of the filter cylinder 28 into a proximal bore portion 62 and a proximal distal bore portion 64. The drip guard 60 limits any contamination originating from the chuck 42 (which presumably has been previously used with another filter cylinder) to the proximal bore portion 62, thereby preventing the cytological material collected on the filter cylinder 28 from being contaminated. That is, any liquid contaminant that drips down from the inner surface of the chuck 42 will be contained by the drip guard 60, and will not be allowed to pass into the distal bore portion 64, where it could otherwise pass through the filter membrane 38. This is especially significant when a positive pressure pulse is conveyed into the bore 36 of the filter cylinder 28, which forces some of the liquid within the distal bore portion 64 to pass through the filter membrane 38.

Referring further to FIGS. 5 and 6, the proximal side of the drip guard 60 comprises an optional recessed cavity 66 in order to facilitate containment of the liquid. Because the pressure within the entire bore 36 must be capable of equalizing in order for the negative and positive pressure pulses applied by the sample processor 14 at the proximal end of the filter cylinder 28 to provide the desired effect at the distal end of the filter cylinder 28, some fluid communication between the proximal and distal bore portions 62 and 64 is required. To this end, the drip guard 60 further comprises access ports 68 (in this case, four equidistantly disposed access ports) through which the proximal and distal bore portions 62 and 64 can fluidly communication with each other. To minimize the possibility that contaminated liquid from the chuck 42 can leak into the distal bore section 64 of the filter cylinder 28, the access ports 68 are disposed around the periphery of the drip guard 60, where liquid is unlikely to drip.

Thus, it can be appreciated that, while the filter cylinder 28 may be discarded, the chuck 42 can be reused with subsequent filter cylinders without the possibility (or at least minimizing the possibility) that the present sample will be contaminated by the chuck 42.

Another way to prevent cross-contamination between samples is to provide a sample collection device that is entirely disposable. In particular, and with reference to FIG. 7, a disposable sample collection device 110 will now be described. The sample collection device 110 is similar to the previously described sample collection device 10, with the exception that the chuck is integrally formed with the filter cylinder as a unibody structure. Specifically, the sample collection device 110 comprises a cylinder 112, a boss 114 integrally formed at the proximal end of the cylinder 112, and a longitudinal bore 114 extending through the cylinder 112 and boss 114. The cylinder 112 and boss 114 are similar to the previously described filter cylinder 28 and boss 52. Because the boss 114 is integrally formed on the cylinder 112, however, there is no need for a cylindrical insert for mating the boss 114 with the cylinder 112. Because the boss 114 is formed of the same inexpensive material as the cylinder 112, the entire sample collection 110 device can be discarded without creating a significantly adverse commercial impact. In addition, no drip guard is needed, since no portion of the sample collection device 110 will be reused.

Although particular embodiments of the invention have been shown and described, it should be understood that the above discussion is not intended to limit the present invention to these embodiments, and it will be obvious to those skilled in the art that various changes and modifications may be made to these embodiments without departing from the scope of the appended claims.

What is claimed:

1. A system for use in the preparation of cytological specimen slides, comprising:
    a sample processor comprising a chuck having an enlarged boss, the boss comprising a recessed cavity configured for engaging a coupling mechanism of the sample processor, the chuck further comprising a cylindrical insert configured for forming a fluid-tight seal around a drip guard of a sample processing cylinder; and
    a sample processing cylinder having a proximal end, a distal rim, and a bore longitudinally extending between the proximal end and the distal rim;
    a filter membrane mounted directly to the distal rim of the cylinder, the membrane having pores in fluid communication with the bore; and
    a drip guard disposed within and in fluid communication with the bore of the cylinder and proximal to the membrane, the drip guard having a plurality of access ports disposed on an outer periphery of the drip guard and in fluid communication with the bore, the drip guard configured for containing a liquid contaminant that drips towards the distal rim of the cylinder, thereby preventing the liquid contaminant from reaching the filter membrane, the drip guard comprising a recessed cavity configured to facilitate containment of the liquid.

2. The system of claim 1, wherein the membrane is configured to collect a layer of cytological material when the bore is subjected to negative pressure.

3. The system of claim 2, wherein the layer of cytological material is a monolayer of cells.

4. The system of claim 1, wherein the drip guard and cylinder are discrete elements.

5. The system of claim 1, wherein the drip guard and cylinder are integrated elements.

* * * * *